US010506942B2

United States Patent
Okada et al.

(10) Patent No.: US 10,506,942 B2
(45) Date of Patent: *Dec. 17, 2019

(54) IN-VIVO SIGNAL SOURCE DETECTION METHOD AND IN-VIVO SIGNAL SOURCE DETECTION DEVICE

(71) Applicants: TORAY ENGINEERING CO., LTD., Tokyo (JP); THE RITSUMEIKAN TRUST, Kyoto (JP)

(72) Inventors: Tatsuya Okada, Shiga (JP); Chisa Inaka, Shiga (JP); Masaaki Makikawa, Kusatsu (JP); Masayasu Yoshiwaki, Kusatsu (JP); Yusuke Sakaue, Shiga (JP)

(73) Assignees: TORAY ENGINEERING CO., LTD., Tokyo (JP); THE RITSUMEIKAN TRUST, Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/324,553

(22) PCT Filed: Jun. 20, 2017

(86) PCT No.: PCT/JP2017/022747
§ 371 (c)(1),
(2) Date: Feb. 9, 2019

(87) PCT Pub. No.: WO2018/034058
PCT Pub. Date: Feb. 22, 2018

(65) Prior Publication Data
US 2019/0175046 A1    Jun. 13, 2019

(30) Foreign Application Priority Data
Aug. 18, 2016 (JP) .................................. 2016-160330

(51) Int. Cl.
*A61B 5/04*      (2006.01)
*A61B 5/0488*    (2006.01)

(52) U.S. Cl.
CPC ........ *A61B 5/0488* (2013.01); *A61B 2562/04* (2013.01)

(58) Field of Classification Search
CPC .......................... A61B 5/0488; A61B 2562/04
See application file for complete search history.

(56) References Cited

U.S. PATENT DOCUMENTS 6,978,170 B1 * 12/2005 Onda ..................... A61B 5/053
                                                                                                    600/547
2017/0354340 A1   12/2017   Matsumura

FOREIGN PATENT DOCUMENTS

| JP | H11-113867 A | 4/1999 |
| JP | 2007-268034 A | 10/2007 |
| WO | 2016/075726 A1 | 5/2016 |

OTHER PUBLICATIONS

International Search Report for corresponding App. No. PCT/JP2017/022747, dated Aug. 8, 2017.

* cited by examiner

*Primary Examiner* — Amanda K Hulbert
*Assistant Examiner* — Natasha Patel
(74) *Attorney, Agent, or Firm* — Renner, Otto, Boisselle & Sklar, LLP

(57) ABSTRACT

In an in-vivo signal source detection method, three electrodes are arranged on the circumference of a surface of an living body to surround multiple muscle fibers; a first voltage $V_i$ generated when a first external resistor is connected to between each electrode and a ground potential and a second voltage $V'_i$ generated when a second external resistor is connected to between each electrode and the ground potential; and a ratio $V_i/V'_i$ is calculated from the first voltage $V_i$ and the second voltage $V'_i$, and the position of a signal source in the living body is detected based on three ratios $V_i/V'_i$.

13 Claims, 13 Drawing Sheets

FIG. 2

| STEP | ELECTRODE | SWITCH SW | $S_1$ | $S_2$ | $S_3$ | OUTPUT |
|---|---|---|---|---|---|---|
| 1 | ch1 | A | C | O | O | $V_1$ |
| 2 | ch2 | A | O | C | O | $V_2$ |
| 3 | ch3 | A | O | O | C | $V_3$ |
| 4 | ch1 | B | C | O | O | $V'_1$ |
| 5 | ch2 | B | O | C | O | $V'_2$ |
| 6 | ch3 | B | O | O | C | $V'_3$ |

C:close(CONDUCTION)
O:open(OPEN)

FIG. 8

| STEP | ELECTRODE | SWITCH SW | $S_1$ | $S_2$ | $S_3$ | $S_{S1}$ | $S_{S2}$ | $S_{S3}$ | OUTPUT |
|---|---|---|---|---|---|---|---|---|---|
| 1 | ch1, ch2 | A | C | O | O | O | C | O | $V_{12}$ |
| 2 | ch2, ch3 | A | O | C | O | O | O | C | $V_{23}$ |
| 3 | ch3, ch1 | A | O | O | C | C | O | O | $V_{31}$ |
| 4 | ch1, ch2 | B | C | O | O | O | C | O | $V'_{12}$ |
| 5 | ch2, ch3 | B | O | C | O | O | O | C | $V'_{23}$ |
| 6 | ch3, ch1 | B | O | O | C | C | O | O | $V'_{31}$ |

C:close(CONDUCTION)
O:open(OPEN)

FIG. 13

| STEP | ELECTRODE | SWITCH SW | $S_{1a}$ | $S_{1b}$ | $S_{2a}$ | $S_{2b}$ | $S_{3a}$ | $S_{3b}$ | OUTPUT |
|---|---|---|---|---|---|---|---|---|---|
| 1 | ch1a, ch1b | A | C | C | O | O | O | O | $V_{1a1b}$ |
| 2 | ch2a, ch2b | A | O | O | C | C | O | O | $V_{2a2b}$ |
| 3 | ch3a, ch3b | A | O | O | O | O | C | C | $V_{3a3b}$ |
| 4 | ch1a, ch1b | B | C | C | O | O | O | O | $V'_{1a1b}$ |
| 5 | ch2a, ch2b | B | O | O | C | C | O | O | $V'_{2a2b}$ |
| 6 | ch3a, ch3b | B | O | O | O | O | C | C | $V'_{3a3b}$ |

C:close(CONDUCTION)
O:open(OPEN)

IN-VIVO SIGNAL SOURCE DETECTION METHOD AND IN-VIVO SIGNAL SOURCE DETECTION DEVICE

TECHNICAL FIELD

The present invention relates to an in-vivo signal source detection method and an in-vivo signal source detection device for detecting the position of an activity site (a signal source) of tissues acting in a living body.

BACKGROUND ART

Measurement of an activity state of tissues acting in a living body has been performed by measurement of a voltage generated at an electrode attached to a surface of the living body.

For example, Patent Document 1 discloses the method for obtaining potential distribution in a section of a living body passing through a predetermined plane by measuring a surface potential at each point on the line of intersection (a closed curve) between the living body and the plane.

CITATION LIST

Patent Document

Patent Document 1: Japanese Unexamined Patent Publication No. H11-113867
Patent Document 2: International Patent Publication No. 2016/075726 A1

SUMMARY OF THE INVENTION

Technical Problem

However, in the method disclosed in Patent Document 1, many electrodes need to be arranged on the living body without clearances for performing measurement, and for this reason, a burden on the living body is great. Moreover, when the number of electrodes is smaller, the burden on the living body is reduced. However, only low-resolution potential distribution can be obtained.

The present invention is intended to provide an in-vivo signal source detection method and an in-vivo signal source detection device for accurately detecting, with a smaller number of electrodes, the position of an activity site (a signal source) of tissues acting in a living body.

Solution to the Problem

An in-vivo signal source detection method according to the present invention is an in-vivo signal source detection method for detecting the position of a signal source in a living body by a voltage generated at an electrode arranged on a surface of the living body. At least three electrodes are arranged on the circumference of the surface of the living body to surround multiple muscle fibers, and a first external resistor and a second external resistor are alternately switchably connected in parallel between each electrode and a ground potential or between ones of the electrodes. A first voltage $V_i$ (i=1, 2, 3) generated when the first external resistor is connected to between each electrode and the ground potential or between ones of the electrodes and a second voltage $V'_i$ (i=1, 2, 3) generated when the second external resistor is connected to between each electrode and the ground potential or between ones of the electrodes are measured. A ratio $V_i/V'_i$ (i=1, 2, 3) is calculated from the first voltage $V_i$ and the second voltage $V'_i$, and the position of the signal source in the living body is detected based on three ratios $V_i/V'_i$ (i=1, 2, 3).

Advantages of the Invention

According to the present invention, the in-vivo signal source detection method and the in-vivo signal source detection device for accurately detecting, with a smaller number of electrodes, the position of an activity site (the signal source) of tissues acting in the living body can be provided.

BRIEF DESCRIPTION OF THE DRAWINGS

FIG. 2 is a table of the steps of switching a connection state between each electrode and an external resistor.
FIG. 8 is a table of the steps of switching a connection state between each electrode and an external resistor.
FIG. 13 is a table of the steps of switching a connection state between each electrode and an external resistor.

DESCRIPTION OF EMBODIMENTS

Figure 1:
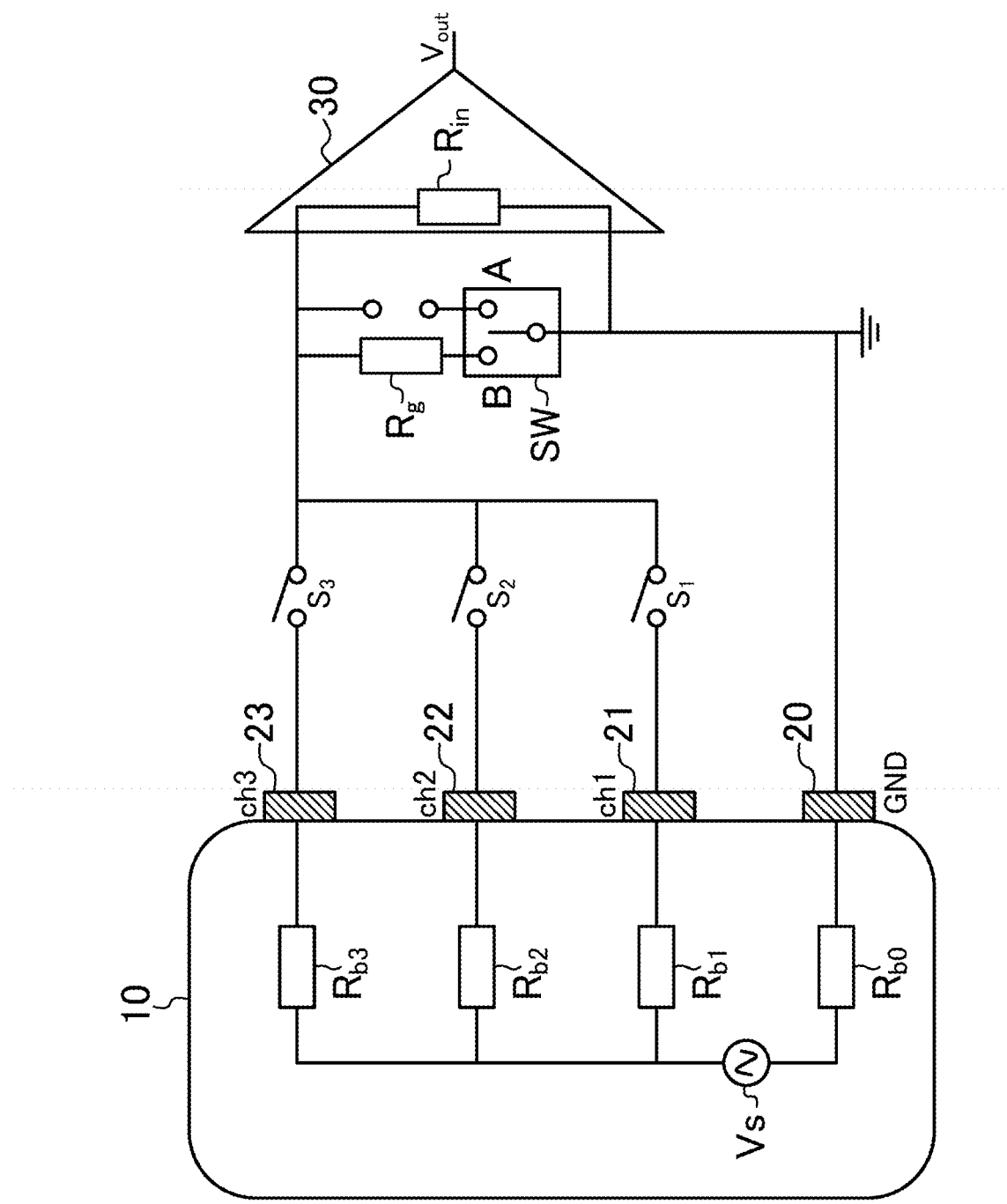
FIG. 1 is an electric network diagram for describing an in-vivo signal source detection method in a first embodiment of the present invention.

Hereinafter, embodiments of the present invention will be described in detail with reference to the drawings. Note that the present invention is not limited to the following embodiments. Various changes may be made without departing from a scope within which the present invention provides advantageous effects. In description below, an "electrode" refers to a member attachable to a surface of a living body, a "potential" refers to an electric level, and a "voltage" refers to a measured electric level, unless otherwise specified.

An applicant of the present application has proposed the method for accurately detecting, with a smaller number of electrodes, the position of an activity site (a signal source) of tissues acting in a living body (Patent Document 2).

In the in-vivo signal source position detection method according to this proposal, at least three electrodes are arranged on a surface of the living body, and two external resistors with different resistance values are connected in parallel between each electrode and a ground potential to measure a voltage $V_i$ (i=1, 2, 3) generated at each electrode when the first external resistor is connected in parallel and a voltage $V'_i$ (i=1, 2, 3) generated at each electrode when the second external resistor is connected in parallel. In this case, when an internal resistance $R_i$ (i=1, 2, 3) between each electrode and the signal source is proportional to a distance $L_i$ (i=1, 2, 3) between each electrode and the signal source, the distance $L_i$ (i=1, 2, 3) can be represented by three simultaneous equations having a voltage ratio $(V_i/V'_i)$ as a variable. Thus, these three simultaneous equations are solved using three measured voltage ratios $(V_i/V'_i)$ so that the three-dimensional coordinates (x, y, z) of the signal source can be obtained.

The equation for obtaining the distance $L_i$ (i=1, 2, 3) includes, as unknown numbers, not only the voltage ratio $(V_i/V'_i)$ as the variable, but also two constants, i.e., a proportional constant between the internal resistance between each electrode and the signal source and the distance between each electrode and the signal source and an internal resistance between the signal source and a ground potential. Thus, for accurately obtaining the position of the signal source by the method of the above-described proposal, these two constants need to be separately obtained.

However, in a case where the method of the above-described proposal is used for the purpose of, e.g., monitoring muscle fibers acting during training, easiness is demanded, and therefore, it is not easy to obtain the above-described two constants in advance. In particular, the proportional constant between the internal resistance and the distance among the above-described constants fluctuates due to influence of tissues in a body, or changes during training. For this reason, it is not easy to accurately obtain this proportional constant in advance.

The invention of the present application has been made in view of the above-described points, and proposes an in-vivo signal source detection method for accurately detecting, with a smaller number of electrodes, the position of an activity site (a signal source) of tissues acting in a living body.

First Embodiment

FIG. 1 is an electric network diagram for describing an in-vivo signal source detection method according to a first embodiment of the present invention.

As illustrated in FIG. 1, three electrodes 21, 22, 23 are arranged on a surface of a living body 10. A first external resistor and a second external resistor configured alternately switchable are connected in parallel between each electrode 21, 22, 23 and a ground potential. In the present embodiment, a resistance value of the first external resistor is infinite, and a resistance value of the second external resistor is Rg. Thus, each electrode 21, 22, 23 and the ground potential are, by a switching section SW, switchable between a case where no external resistor Rg is connected and a case where the external resistor Rg is connected. Note that in the present embodiment, although a ground electrode 20 is arranged on the surface of the living body 10 to serve as the ground potential, the ground electrode 20 is not necessarily arranged on the surface of the living body 10.

Note that in the present embodiment, the ground electrode 20 is arranged on the surface of the living body 10, and serves as the ground potential by connection of the ground electrode 20 to an in-vivo signal source detection device.

A voltage originating from a signal source Vs in the living body 10 is generated at each electrode 21, 22, 23 arranged on the surface of the living body 10. The voltage is amplified by an amplifier 30, and then, is outputted as an output voltage Vout. A switch $S_1$, $S_2$, $S_3$ is arranged between each electrode 21, 22, 23 and the amplifier 30. By sequentially bringing the switches $S_1$, $S_2$, $S_3$ into conduction, the voltage generated at each electrode 21, 22, 23 is measured as the output voltage Vout of the amplifier 30.

In the present embodiment, as illustrated in FIG. 2, the switching section SW and the switches $S_1$, $S_2$, $S_3$ are each switched (steps 1 to 6). In this manner, first voltages $V_1$, $V_2$, $V_3$ each generated at the electrodes 21, 22, 23 when no external resistor is connected to between each electrode 21, 22, 23 and the ground potential and second voltages $V'_1$, $V'_2$, and $V'_3$ each generated at the electrodes 21, 22, 23 when the external resistor Rg is connected to between each electrode 21, 22, 23 and the ground potential are measured. Note that in FIG. 2, the electrodes 21, 22, 23 are each indicated as channels $ch_1$, $ch_2$, and $ch_3$.

Figure 3:
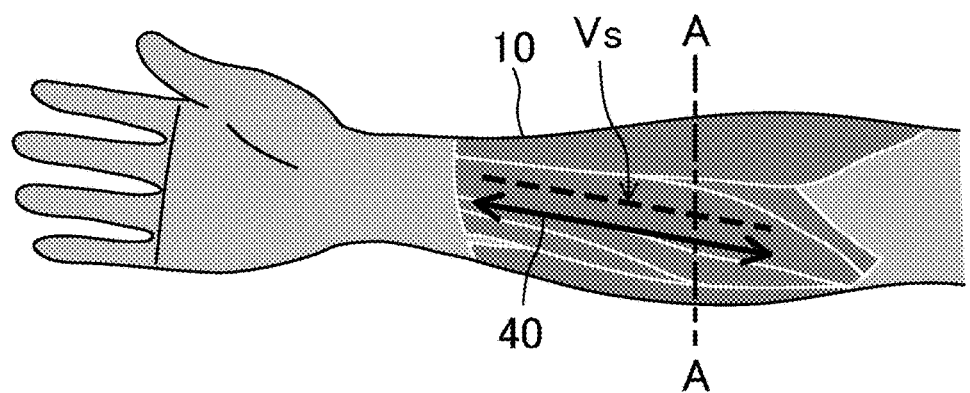
FIG. 3 is a view of a model of a signal source as a detection target.

FIG. 3 is a view of a model of a signal source as a detection target in the present embodiment.

The model of the signal source illustrated in FIG. 3 is multiple muscle fibers 40 forming, e.g., a skeletal muscle of an arm, and each muscle fiber 40 is linearly present along the direction of an arrow in the figure. When the skeletal muscle acts (contracts), a particular muscle fiber 40 serves as the signal source Vs, and generates a high potential. An activity site of the muscle fiber 40 as the signal source Vs is linearly present along the direction of the muscle fiber 40, and therefore, potential distribution at the signal source Vs is uniform. Thus, as illustrated in FIG. 3, when a detection area for the signal source Vs is limited to the inside of a section along an A-A line, the linear signal source Vs can be taken as a point of two-dimensional coordinates (x, y).

Figure 4:
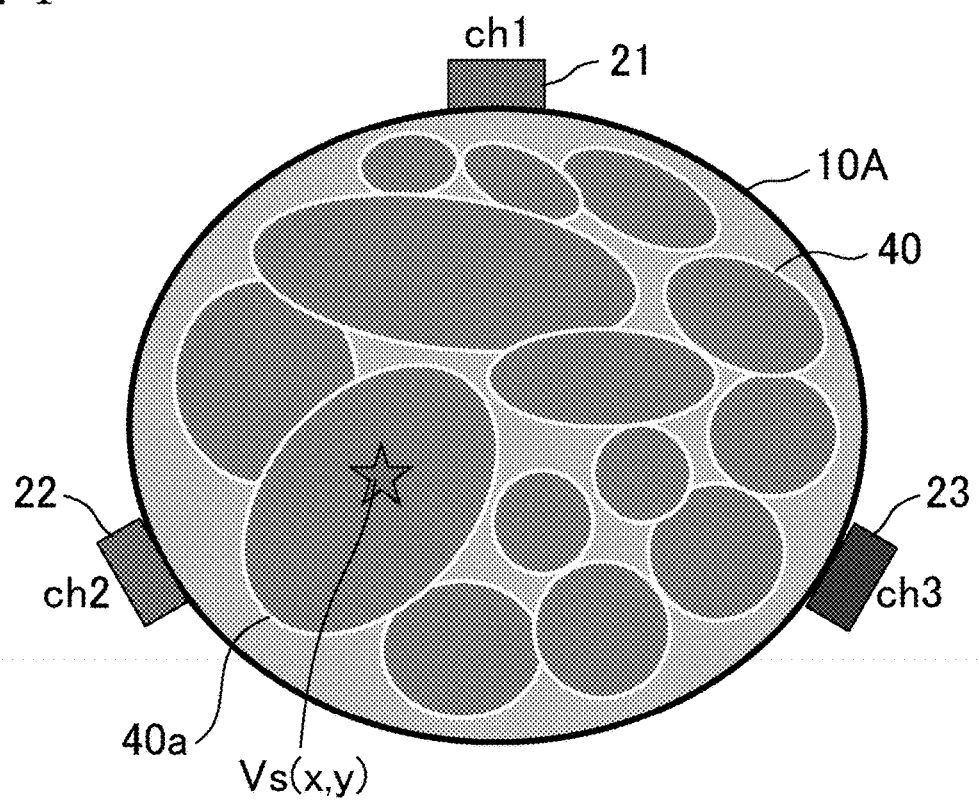
FIG. 4 is a view of arrangement of the electrodes on a surface of a living body.

Based in the above-described finding, three electrodes 21, 22, 23 are arranged on a circumference 10A of the surface of the living body 10 to surround the multiple muscle fibers 40 as illustrated in FIG. 4 in the in-vivo signal source detection method according to the present embodiment. Moreover, an activity site 40a of the muscle fiber 40 as the signal source Vs is detected as the point of the two-dimensional coordinates (x, y).

Hereinafter, a specific method for detecting the position (x, y) of the signal source Vs will be described with reference to FIGS. 5 and 6.

Figure 5:
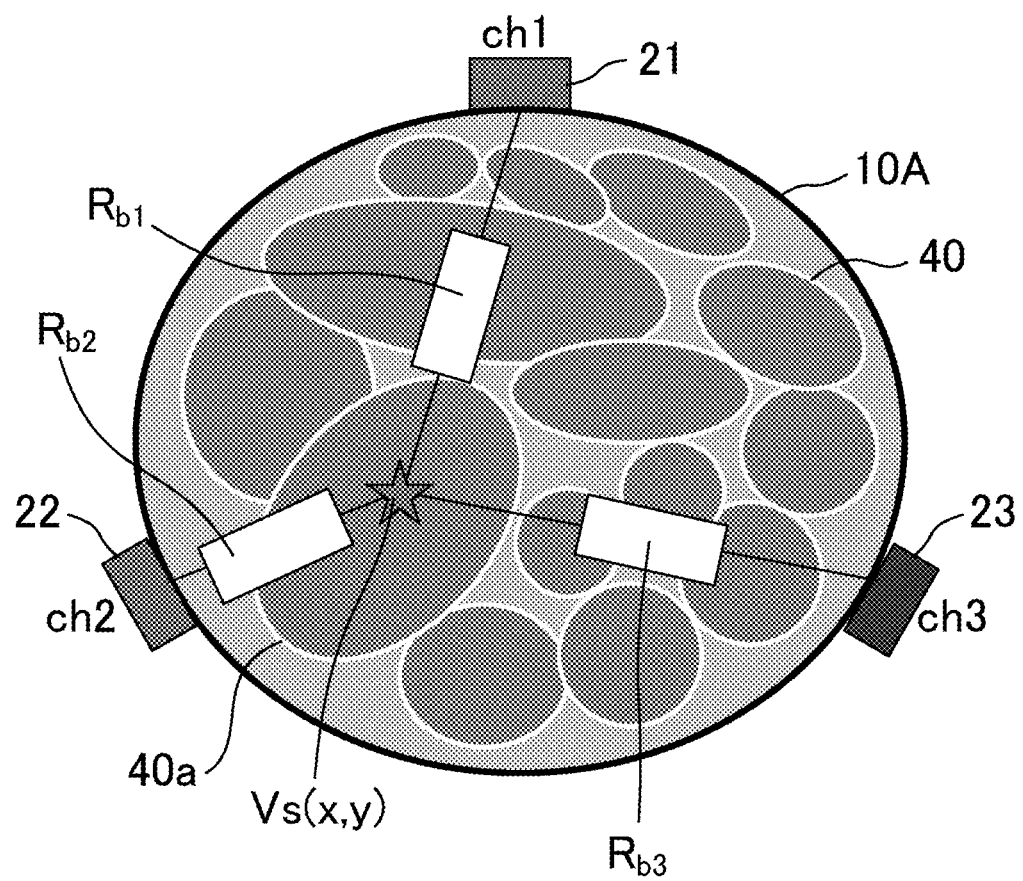
FIG. 5 is a view for describing the method for detecting the position of the signal source.
Figure 6:
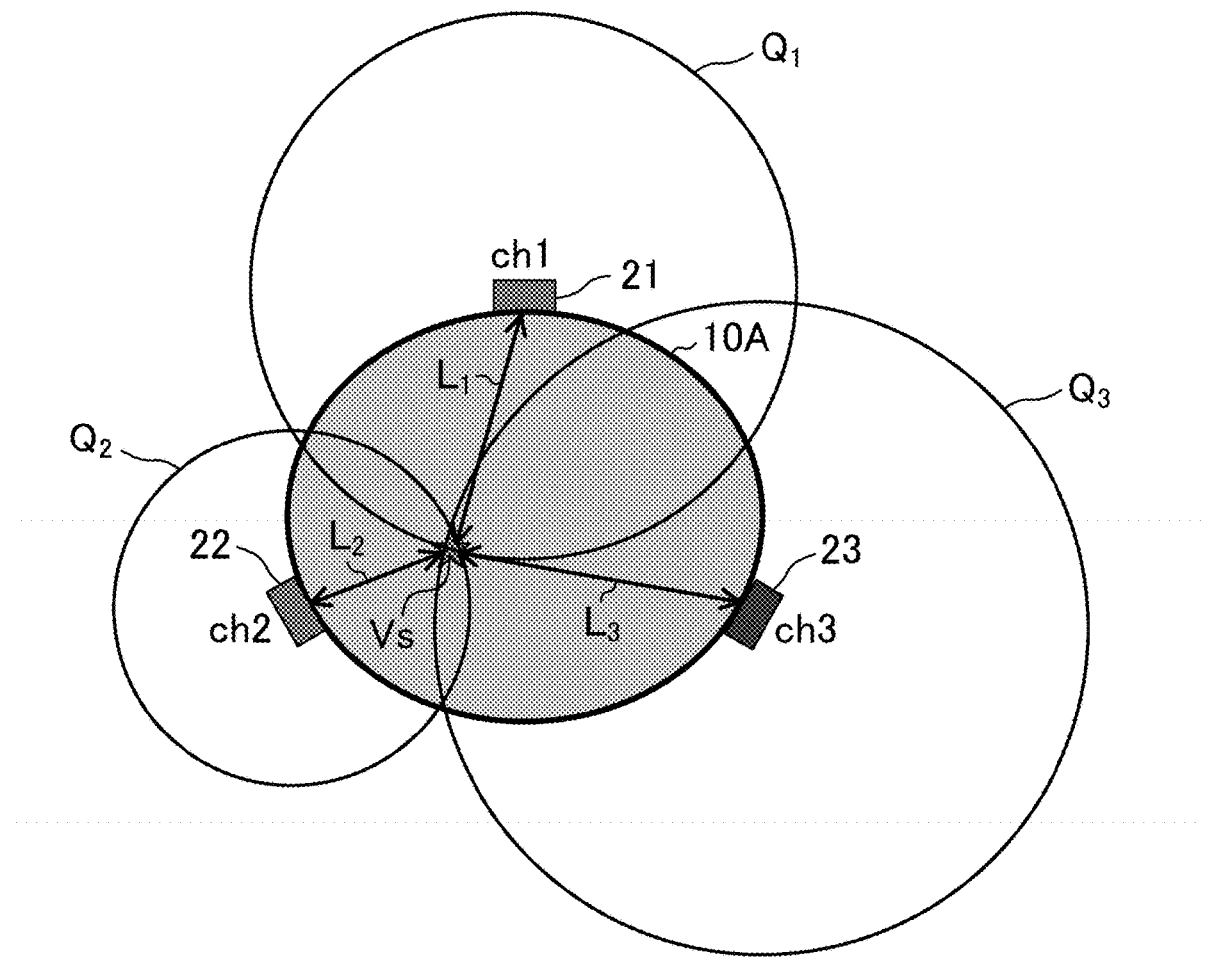
FIG. 6 is a view for describing the method for detecting the position of the signal source.

FIG. 5 is a view when three electrodes 21, 22, 23 are arranged on the circumference 10A of the surface of the living body 10 to surround the multiple muscle fibers 40, and an internal resistor between the signal source Vs and each electrode 21, 22, 23 is represented by $R_{b1}$, $R_{b2}$, $R_{b3}$.

In this case, at the step 1, the first voltage (when no external resistor is connected) $V_1$ generated at the electrode 21 (the channel $ch_1$) is given by Equation (1-1).

[Equation 1]

$$V_{out}=V_1=V_S \qquad \text{(Equation 1-1)}$$

On the other hand, at the step 4, the second voltage (when the external resistor Rg is connected) $V'_1$ generated at the electrode 21 (the channel $ch_1$) is given by Equation (1-2) if an input resistance $R_{in}$ of the amplifier 30 is extremely high.

[Equation 2]

$$V_{out} = V'_1 = \frac{R_g}{R_{b1} + R_{b0} + R_g} V_s \quad \text{(Equation 1-2)}$$

In this equation, $R_{b0}$ represents an internal resistance between the signal source Vs and the ground electrode 20.

From Equations (1), (2), a ratio (an attenuation ratio) $V'_1/V_1$ between the first voltage $V_1$ generated at the electrode 21 (the channel $ch_1$) when no external resistor Rg is connected and the second voltage $V'_1$ generated at the electrode 21 (the channel $ch_1$) when the external resistor Rg is connected is given by Equation (1-3).

[Equation 3]

$$\frac{V'_1}{V_1} = \frac{R_g}{R_{b1} + R_{b0} + R_g} \quad \text{(Equation 1-3)}$$

Similarly, a ratio (an attenuation ratio) $V'_2/V_2$ between the first voltage $V_2$ generated at the electrode 22 (the channel $ch_2$) when no external resistor Rg is connected and the second voltage $V'_2$ generated at the electrode 22 (the channel $ch_2$) when the external resistor Rg is connected and a ratio (an attenuation ratio) $V'_3/V_3$ between the first voltage $V_3$ generated at the electrode 23 (the channel $ch_3$) when no external resistor Rg is connected and the second voltage $V'_3$ generated at the electrode 23 (the channel $ch_3$) when the external resistor Rg is connected are each given by Equations (1-4), (1-5).

[Equation 4]

$$\frac{V'_2}{V_2} = \frac{R_g}{R_{b2} + R_{b0} + R_g} \quad \text{(Equation 1-4)}$$

[Equation 5]

$$\frac{V'_3}{V_3} = \frac{R_g}{R_{b3} + R_{b0} + R_g} \quad \text{(Equation 1-5)}$$

Assuming that conductivity inside the living body 10 is uniform, each internal resistance value $R_{b1}$, $R_{b2}$, $R_{b3}$ is considered to be proportional to a distance between the signal source Vs in the living body 10 and the electrode 21, 22, 23. Thus, from Equations (1-3), (1-4), (1-5), the distances $L_1$, $L_2$, and $L_3$ between the signal source Vs in the living body 10 and each electrode 21, 22, 23 are each given by Equations (1-6), (1-7), (1-8).

[Equation 6]

$$L_1 = \beta R_{b1} = \beta\left\{\left(\frac{V_1}{V'_1} - 1\right)R_g - R_{b0}\right\} \quad \text{(Equation 1-6)}$$

[Equation 7]

$$L_2 = \beta R_{b2} = \beta\left\{\left(\frac{V_2}{V'_2} - 1\right)R_g - R_{b0}\right\} \quad \text{(Equation 1-7)}$$

[Equation 8]

$$L_3 = \beta R_{b3} = \beta\left\{\left(\frac{V_3}{V'_3} - 1\right)R_g - R_{b0}\right\} \quad \text{(Equation 1-8)}$$

In these equations, $\beta$ is a proportional constant between an internal resistance $R_{bi}$ and a distance $L_i$ (i=1, 2, 3), and is defined by the conductivity of the living body 10, for example.

As shown in Equations (1-6), (1-7), (1-8), each of the distances $L_1$, $L_2$, $L_3$ is expressed as the function of the reciprocal of the attenuation ratio ($V'_1/V_1$, $V'_2/V_2$, $V'_3/V_3$). As illustrated in FIG. 6, the signal source Vs is considered to be present at the point of intersection of three circles $Q_1$, $Q_2$, $Q_3$ each having radiuses $L_1$, $L_2$, $L_3$ about the electrodes 21, 22, 23. When the position coordinates of each electrode 21, 22, 23 is $(a_1, b_1)$, $(a_2, b_2)$, $(a_3, b_3)$, the circles $Q_1$, $Q_2$, $Q_3$ are each represented by the following equations (1-9), (1-10), (1-11).

[Equation 9]

$$\sqrt{(x-a_1)^2+(y-b_1)^2}=L_1 \quad \text{(Equation 1-9)}$$

[Equation 10]

$$\sqrt{(x-a_2)^2+(y-b_2)^2}=L_2 \quad \text{(Equation 1-10)}$$

[Equation 11]

$$\sqrt{(x-a_3)^2+(y-b_3)^2}=L_3 \quad \text{(Equation 1-11)}$$

Thus, using $L_1$, $L_2$, $L_3$ obtained from Equations (1-6), (1-7), (1-8), the above-described equations (1-9), (1-10), (1-11) are three simultaneous equations represented by the following equation (1-12).

[Equation 12]

$$\sqrt{(x-a_1)^2+(y-b_1)^2} = \beta\left\{\left(\frac{V_1}{V'_1}-1\right)R_g-R_{b0}\right\} \quad \text{(Equation 1-12)}$$
$$\sqrt{(x-a_2)^2+(y-b_2)^2} = \beta\left\{\left(\frac{V_2}{V'_2}-1\right)R_g-R_{b0}\right\}$$
$$\sqrt{(x-a_3)^2+(y-b_3)^2} = \beta\left\{\left(\frac{V_3}{V'_3}-1\right)R_g-R_{b0}\right\}$$

Unknown numbers of three simultaneous equations represented by Equation (1-12) are four numbers including the two-dimensional coordinates (x, y) of the signal source Vs, the constant $\beta$, and $R_{b0}$. Thus, three simultaneous equations are solved using a given value of $R_{b0}$ so that the two-dimensional coordinates (x, y) of the signal source Vs and the constant $\beta$ can be obtained.

According to the present embodiment, the external resistor is connected in parallel between each of three electrodes 21, 22, 23 arranged on the surface of the living body 10 and the ground potential, and the ratio (the attenuation ratio) of the voltage generated at each electrode 21, 22, 23 is measured by switching of a connection state between these components. In this manner, the two-dimensional coordinates (x, y) of the signal source Vs can be easily detected. Thus, the two-dimensional position of the signal source Vs in the living body can be accurately detected with a smaller number of electrodes.

Moreover, according to the present embodiment, the proportional constant $\beta$ between the internal resistance $R_{bi}$ and the distance $L_i$ (i=1, 2, 3) can be obtained in such a manner that the above-described simultaneous equations are solved. Thus, even when the proportional constant β fluctuates due to influence of a body tissue or changes during detection, the two-dimensional position of the signal source Vs in the living body can be more accurately detected. In particular, even in the case of, e.g., monitoring muscle fibers acting during training, the muscle fibers acting in the living body can be easily detected.

Note that in the present embodiment, description has been made assuming that there is one signal source Vs in the living body 10. However, multiple signal sources might be actually generated at once. Even in this case, according to the present embodiment, a most dominant one of electric signals of these signal sources can be obtained as the signal source.

Moreover, in the present embodiment, the switching section SW and the switches $S_1$, $S_2$, $S_3$ are, as illustrated in FIG. 2, switched to sequentially measure the first voltages $V_1$, $V_2$, $V_3$ and the second voltages $V'_1$, $V'_2$, $V'_3$ at the electrodes 21, 22, 23. Thus, there is a probability that an error is caused in measurement of the position of the signal source Vs when the potential of the signal source Vs changes within switching time. For this reason, switching of each electrode and the external resistor is preferably performed as fast as possible. For example, switching is preferably performed at equal to or shorter than 1 μs, and more preferably at equal to or shorter than 0.1 μs.

Note that in the present embodiment, the resistance value of the first external resistor is infinite (non-conduction), and the resistance value of the second external resistor is Rg. However, the first external resistor may be a resistance value different from that of the second external resistor.

In this case, in the in-vivo signal source detection method according to the present embodiment, three electrodes 21, 22, 23 are arranged on the circumference of the surface of the living body 10, and the first external resistor and the second external resistor configured alternately switchable are connected in parallel between each electrode 21, 22, 23 and the ground potential. Moreover, a first voltage $V_i$ (i=1, 2, 3) generated at each electrode 21, 22, 23 when the first external resistor is connected in parallel between each electrode 21, 22, 23 and the ground potential and a second voltage $V'_i$ (i=1, 2, 3) generated at each electrode 21, 22, 23 when the second external resistor is connected in parallel between each electrode 21, 22, 23 and the ground potential are measured. Further, the ratio $V_i/V'_i$ (i=1, 2, 3) may be calculated from the first voltage $V_i$ and the second voltage $V'_i$, and the position of the signal source Vs in the living body may be detected based on these three ratios $V_i/V'_i$ (i=1, 2, 3).

As described above, at the steps 1 to 6 of the in-vivo signal source detection method according to the present embodiment, the ratio $V_i/V'_i$ (i=1, 2, 3) between the first voltage $V_i$ (i=1, 2, 3) and the second voltage $V'_i$ (i=1, 2, 3) at each electrode 21, 22, 23 is calculated, and the two-dimensional position of the signal source Vs in the living body is detected based on these three ratios $V_i/V'_i$ (i=1, 2, 3). Thus, measurement of the voltage ratios $V_i/V'_i$ (i=1, 2, 3) at the steps 1 to 6 is taken as a single cycle, and such a cycle is repeated so that fluctuation in the signal source Vs in the living body can be detected in real time from time-series voltage ratio measurement data in each cycle. For example, in the case of monitoring muscle fibers acting during training, the muscle fibers acting in response to movement of a skeletal muscle can be detected in real time.

FIG. 1 illustrates the in-vivo signal source detection device in the present embodiment.

As illustrated in FIG. 1, the in-vivo signal source detection device in the present embodiment includes at least three electrodes 21, 22, 23 arranged on the circumference of the surface of the living body 10, and a connection section configured to alternately switch the first external resistor and the second external resistor to connect the first external resistor or the second external resistor in parallel between each electrode 21, 22, 23 and the ground potential. For example, as illustrated in FIG. 1, the switching section SW, the switches $S_1$, $S_2$, $S_3$, etc. can be used as the connection section. Moreover, the in-vivo signal source detection device includes a measurement section (the amplifier) 30 configured to measure, in a state in which each electrode 21, 22, 23 is arranged on the surface of the living body 10, the first voltage $V_i$ (i=1, 2, 3) generated at each electrode when the connection section switches the first external resistor to parallel connection between each electrode 21, 22, 23 and the ground potential and the second voltage $V'_i$ (i=1, 2, 3) generated at each electrode when the connection section switches the second external resistor to parallel connection between each electrode 21, 22, 23 and the ground potential. Further, the in-vivo signal source detection device includes a detection section (not shown) configured to calculate the ratios $V_i/V'_i$ (i=1, 2, 3) from the first voltages $V_i$ and the second voltages $V'_i$, thereby detecting the position of the signal source in the living body based on these three ratios $V_i/V'_i$ (i=1, 2, 3). Note that the detection section may include, for example, a CPU configured to perform arithmetic processing for measurement data from the amplifier 30.

Second Embodiment

Figure 7:
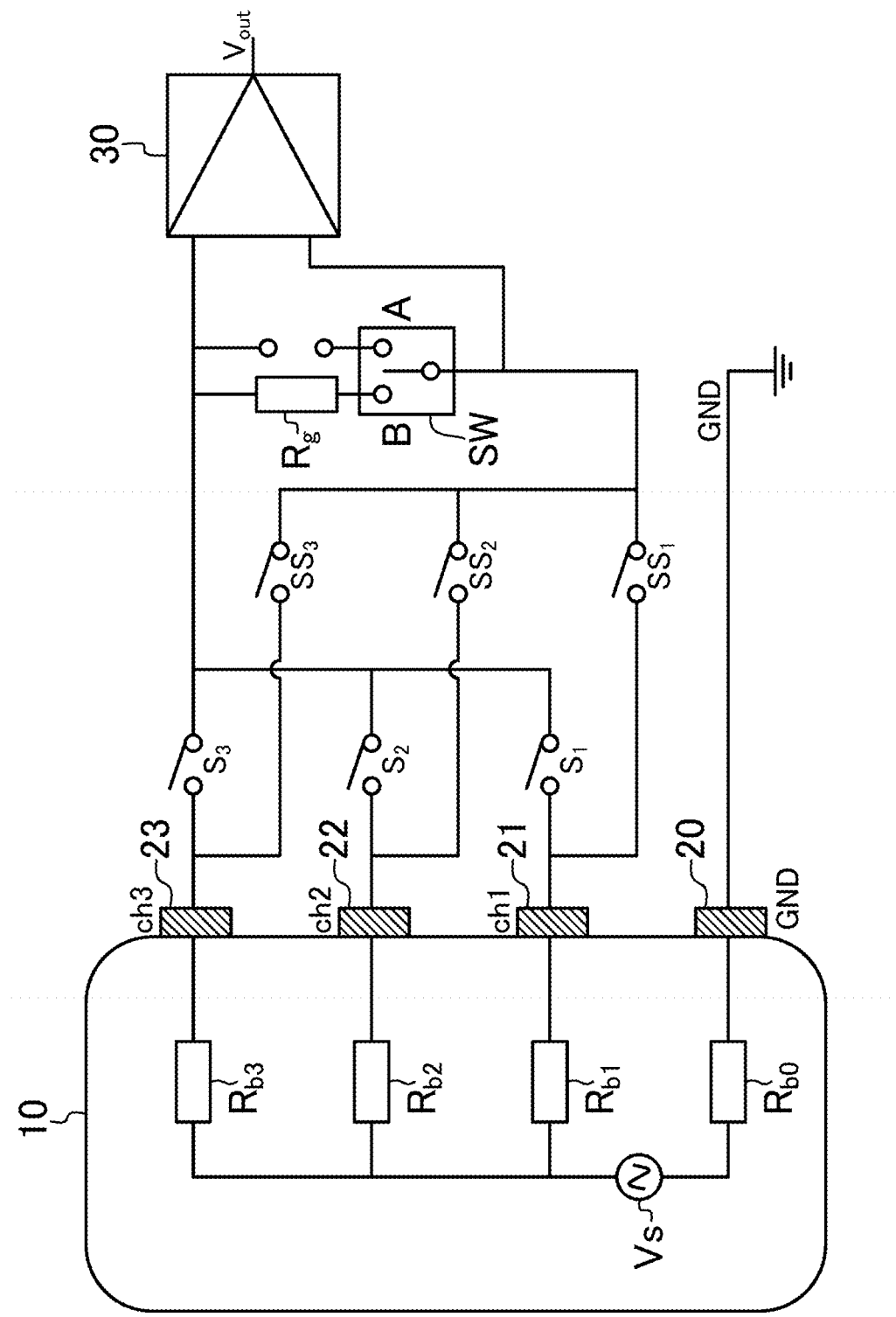
FIG. 7 is an electric network diagram for describing an in-vivo signal source detection method in a second embodiment of the present invention.

FIG. 7 is an electric network diagram for describing an in-vivo signal source detection method in a second embodiment of the present invention.

As illustrated in FIG. 7, three electrodes 21, 22, 23 are arranged on a surface of a living body 10. Note that in the present embodiment, three electrodes 21, 22, 23 are arranged on a circumference 10A of the surface of the living body 10 to surround multiple muscle fibers 40 as in the first embodiment illustrated in FIG. 4. Moreover, a first external resistor and a second external resistor configured alternately switchable are connected in parallel between the first electrode 21 and the second electrode 22, between the second electrode 22 and the third electrode 23, and between the third electrode 23 and the first electrode 21. Note that in the present embodiment, a resistance value of the first external resistor is, as in the first embodiment, infinite and a resistance value of the second external resistor is Rg. Moreover, in the present embodiment, a ground electrode 20 is, as in the first embodiment, arranged on the surface of the living body 10 to serve as a ground potential.

As illustrated in FIG. 7, a switch $S_1$, $S_2$, $S_3$ and a switch $SS_1$, $SS_2$, $SS_3$ are arranged between each electrode 21, 22, 23 and a difference amplifier 30. By sequentially bringing the switches $S_1$, $S_2$, $S_3$, $SS_1$, $SS_2$, $SS_3$ into conduction as illustrated in FIG. 8, voltages generated between the first electrode 21 and the second electrode 22, between the second electrode 22 and the third electrode 23, and between the third electrode 23 and the first electrode 21 are measured as an output voltage Vout of the difference amplifier 30. The electrodes are, by a switching section SW, switchable between a case where no external resistor is connected and a case where the external resistor Rg is connected. Thus, each of the switching section SW and the switches $S_1$, $S_2$, $S_3$, $SS_1$, $SS_2$, $SS_3$ is switched as illustrated in FIG. 8 (steps 1 to 6), and in this manner, first voltages $V_{12}$, $V_{23}$, $V_{31}$ each generated between the electrodes when no external resistor Rg is connected between the electrodes and second voltages $V'_{12}$, $V'_{23}$, $V'_{31}$ each generated between the electrodes when the external resistor Rg is connected between the electrodes are measured. Note that in FIG. 7, the electrodes 21, 22, 23 are each indicated as channels $ch_1$, $ch_2$, and $ch_3$.

At the step 1 illustrated in FIG. 8, the first voltage (when no external resistor is connected) $V_{12}$ generated between the electrode 21 and the electrode 22 (between the channels $ch_1$, $ch_2$) is given by Equation (2-1).

[Equation 13]

$$V_{out}=V_{12}=V_s \quad \text{(Equation 2-1)}$$

On the other hand, at the step 4, the second voltage (when the external resistor Rg is connected) $V'_{12}$ generated between the electrode 21 and the electrode 22 (between the channels $ch_1$, $ch_2$) is given by Equation (2-2) if an input resistance $R_{in}$ of the amplifier 30 is extremely high.

[Equation 14]

$$V_{out} = V'_{12} = \frac{R_g}{R_{b1} + R_{b2} + R_g} V_s \quad \text{(Equation 2-2)}$$

In this equation, $R_{b1}$ and $R_{b2}$ represent an internal resistance between a signal source Vs in the living body 10 and the electrode 21 (the channel $ch_1$) and an internal resistance between the signal source Vs and the electrode 22 (the channel $ch_2$).

From Equations (2-1), (2-2), a ratio (an attenuation ratio) $V'_{12}/V_{12}$ between the first voltage $V_{12}$ and the second voltage $V'_{12}$ generated between the electrode 21 and the electrode 22 (between the channels $ch_1$, $ch_2$) is given by Equation (2-3).

[Equation 15]

$$\frac{V'_{12}}{V_{12}} = \frac{R_g}{R_{b1} + R_{b2} + R_g} \quad \text{(Equation 2-3)}$$

Similarly, a ratio (an attenuation ratio) $V'_{23}/V_{23}$ between the first voltage $V_{23}$ and the second voltage $V'_{23}$ generated between the electrode 22 and the electrode 23 (between the channels $ch_2$, $ch_3$) and a ratio (an attenuation ratio) $V'_{31}/V_{31}$ between the first voltage $V_{31}$ and the second voltage $V'_{31}$ generated between the electrode 23 and the electrode 21 (between the channels $ch_3$, $ch_1$) are each given by Equations (2-4), (2-5).

[Equation 16]

$$\frac{V'_{23}}{V_{23}} = \frac{R_g}{R_{b2} + R_{b3} + R_g} \quad \text{(Equation 2-4)}$$

[Equation 17]

$$\frac{V'_{31}}{V_{31}} = \frac{R_g}{R_{b3} + R_{b1} + R_g} \quad \text{(Equation 2-5)}$$

In these equations, $R_{b3}$ represents an internal resistance value between the signal source Vs in the living body 10 and the electrode 23 ($ch_3$).

In measurement of the voltage generated between the electrodes, an internal resistance in the living body 10 is represented by the sum of internal resistances between each electrode and the signal source. For example, in measurement of the first voltage $V_{12}$ and the second voltage $V'_{12}$ generated between the electrode 21 and the electrode 22 (between the channels $ch_1$, $ch_2$), the internal resistance in the living body 10 is represented by $R_{b1}+R_{b2}$.

Assuming that conductivity inside the living body 10 is uniform, the sum of the internal resistances ($R_{b1}+R_{b2}$) is considered to be proportional to the sum ($D_1+D_2$) of a distance $D_1$ between the electrode 21 and the signal source Vs and a distance $D_2$ between the electrode 22 and the signal source Vs. Thus, from Equations (2-3), (2-4), (2-5), the sums ($D_1+D_2$), ($D_2+D_3$), ($D_3+D_1$) of the distances between each electrode and the signal source Vs are each given by Equations (2-6), (2-7), (2-8).

[Equation 18]

$$D_1 + D_2 = \alpha(R_{b1} + R_{b2}) = \alpha\left(\frac{V_{12}}{V'_{12}} - 1\right)R_g \quad \text{(Equation 2-6)}$$

[Equation 19]

$$D_2 + D_3 = \alpha(R_{b2} + R_{b3}) = \alpha\left(\frac{V_{23}}{V'_{23}} - 1\right)R_g \quad \text{(Equation 2-7)}$$

[Equation 20]

$$D_3 + D_1 = \alpha(R_{b3} + R_{b1}) = \alpha\left(\frac{V_{31}}{V'_{31}} - 1\right)R_g \quad \text{(Equation 2-8)}$$

In these equations, α is a proportional constant between an internal resistance $R_{bi}$ and a distance $D_i$ (i=1, 2, 3), and is defined by the conductivity of the living body 10, for example.

Figure 9:
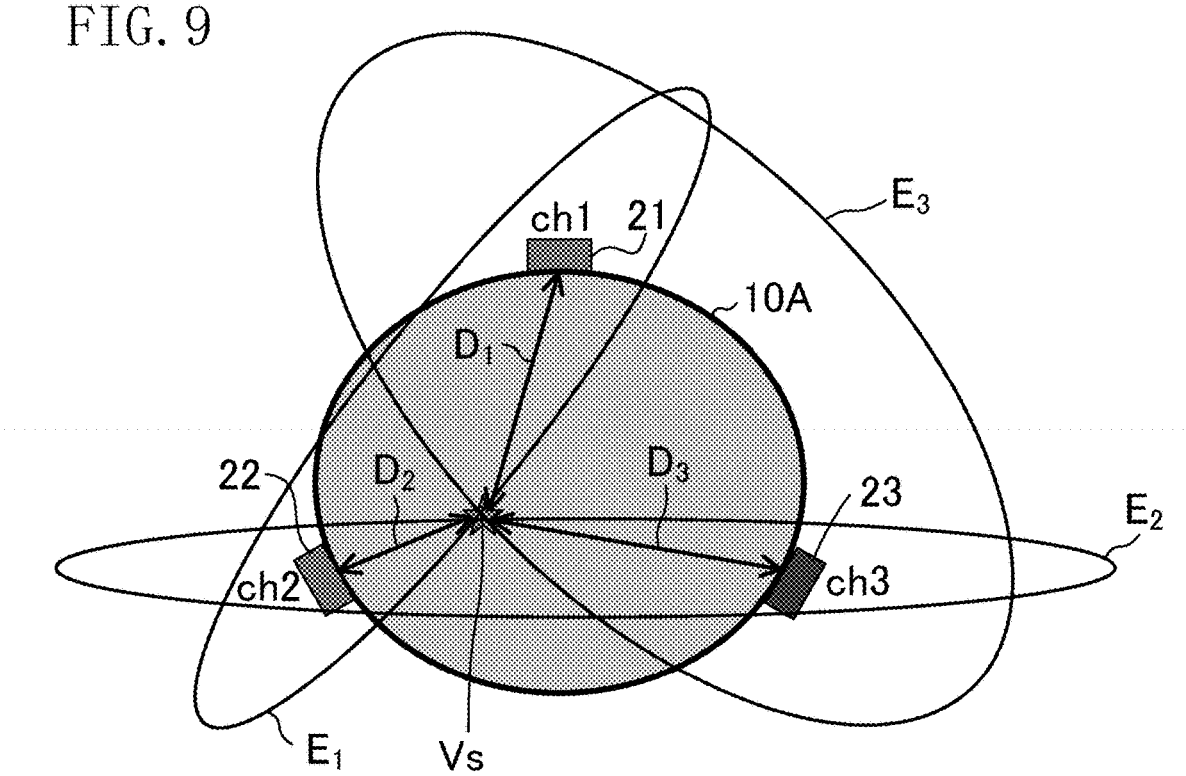
FIG. 9 is a view for describing the method for detecting the position of a signal source.

As shown in Equations (2-6), (2-7), (2-8), each of the sums ($D_1+D_2$), ($D_2+D_3$), ($D_3+D_1$) of the distances between each electrode and the signal source Vs is expressed as the function of the reciprocal of the attenuation ratio ($V'_{12}/V_{12}$, $V'_{23}/V_{23}$, $V'_{31}/V_{31}$). As illustrated in FIG. 9, the signal source Vs is considered to be present at the point of intersection of an ellipse $E_1$ having focal points at the electrodes 21, 22 (the channels $ch_1$, $ch_2$), an ellipse $E_2$ having focal points at the electrodes 22, 23 (the channels $ch_2$, $ch_3$), and an ellipse $E_3$ having focal points at the electrodes 23, 21 (the channels $ch_3$, $ch_1$).

When the position coordinates of each electrode 21, 22, 23 are ($a_1$, $b_1$), ($a_2$, $b_2$), ($a_3$, $b_3$), the ellipses $E_1$, $E_2$, $E_3$ are each represented by the following equations (2-9), (2-10), (2-11).

[Equation 21]

$$\sqrt{(x-a_1)^2+(y-b_1)^2}+\sqrt{(x-a_2)^2+(y-b_2)^2}=D_1+D_2 \quad \text{(Equation 2-9)}$$

[Equation 22]

$$\sqrt{(x-a_2)^2+(y-b_2)^2}+\sqrt{(x-a_3)^2+(y-b_3)^2}=D_2+D_3 \quad \text{(Equation 2-10)}$$

[Equation 23]

$$\sqrt{(x-a_3)^2+(y-b_3)^2}+\sqrt{(x-a_1)^2+(y-b_1)^2}=D_3+D_1 \quad \text{(Equation 2-11)}$$

Thus, using $(D_1+D_2)$, $(D_2+D_3)$, and $(D_3+D_1)$ obtained from Equations (2-6), (2-7), (2-8), three simultaneous equations represented by the following equation (2-12) are solved so that the two-dimensional coordinates (x, y) of the signal source Vs can be obtained.

[Equation 24]

$$\sqrt{(x-a_1)^2+(y-b_1)^2} + \sqrt{(x-a_2)^2+(y-b_2)^2} = \alpha\left(\frac{V_{12}}{V'_{12}}-1\right)R_g$$

$$\sqrt{(x-a_2)^2+(y-b_2)^2} + \sqrt{(x-a_3)^2+(y-b_3)^2} = \alpha\left(\frac{V_{23}}{V'_{23}}-1\right)R_g$$

$$\sqrt{(x-a_3)^2+(y-b_3)^2} + \sqrt{(x-a_1)^2+(y-b_1)^2} = \alpha\left(\frac{V_{31}}{V'_{31}}-1\right)R_g$$

(Equation 2-12)

Unlike the simultaneous equations (1-12) described in the first embodiment, Equation (2-12) does not include, according to the present embodiment, an internal resistance $R_{b0}$ between the signal source Vs and the ground electrode 20. Moreover, unknown numbers of three simultaneous equations represented by Equation (2-12) are three numbers including the two-dimensional coordinates (x, y) of the signal source Vs and the constant α. Thus, three simultaneous equations represented by Expression (2-12) are solved so that the two-dimensional coordinates (x, y) of the signal source Vs and the constant α can be obtained.

As described above, according to the present embodiment, when the two-dimensional coordinates (x, y) of the signal source Vs are obtained, two constants, i.e., the proportional constant α between the internal resistance $R_{bi}$ and the distance $D_i$ (i=1, 2, 3) and the internal resistance $R_{b0}$ between the signal source Vs and the ground electrode 20, are not necessarily obtained in advance, and the two-dimensional coordinates of the signal source Vs in the living body can be easily obtained. In particular, even in the case of, e.g., monitoring muscle fibers acting during training, the muscle fibers acting in the living body can be easily detected.

FIG. 7 illustrates a configuration of an in-vivo signal source detection device in the present embodiment.

As illustrated in FIG. 7, the in-vivo signal source detection device in the present embodiment includes at least three electrodes 21, 22, 23 arranged on the circumference of the surface of the living body 10, and a connection section configured to alternately switch the first external resistor and the second external resistor to connect the first external resistor or the second external resistor in parallel between the first electrode 21 and the second electrode 22, between the second electrode 22 and the third electrode 23, and between the third electrode 23 and the first electrode 21. Moreover, the in-vivo signal source detection device includes a measurement section (the amplifier) 30 configured to measure, in a state in which each electrode 21, 22, 23 is arranged on the surface of the living body 10, the first voltages $V_{12}$, $V_{23}$, $V_{31}$ each generated between the electrodes when the connection section switches the first external resistor to parallel connection between the electrodes and the second voltages $V'_{12}$, $V'_{23}$, $V'_{31}$ each generated between the electrodes when the connection section switches the second external resistor to parallel connection between the electrodes. Further, the in-vivo signal source detection device includes a detection section configured to calculate the ratios $V_{12}/V'_{12}$, $V_{21}/V'_{21}$, $V_{31}/V'_{31}$ from the first voltages $V_{12}$, $V_{23}$, $V_{31}$ and the second voltages $V'_{12}$, $V'_{23}$, $V'_{31}$, thereby detecting the position of the signal source in the living body based on these three ratios $V_{12}/V'_{12}$, $V_{21}/V'_{21}$, $V_{31}/V'_{31}$.

Third Embodiment

Figure 10:
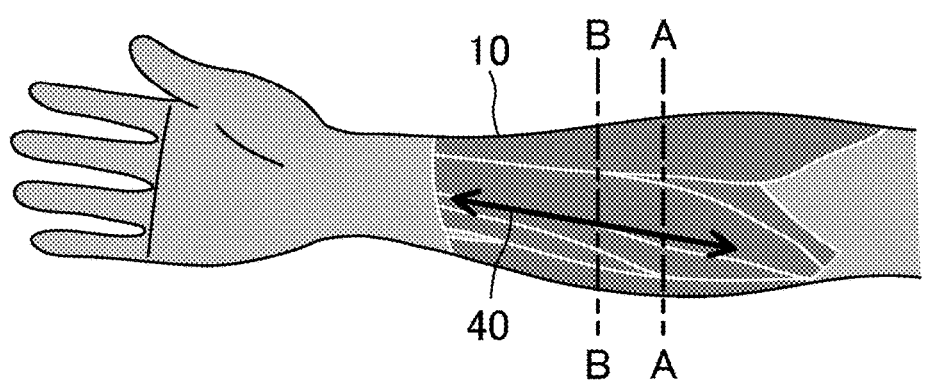
FIG. 10 is a view of a model of the signal source as a detection target.

FIG. 10 is a view of multiple muscle fibers 40 forming, e.g., a skeletal muscle of an arm as a model of a signal source in a third embodiment of the present invention, and each muscle fiber 40 is linearly present along the direction of an arrow in the figure. Moreover, FIG. 11 is a conceptual diagram illustrating, as a cylinder having a center axis parallel to the direction of the muscle fiber 40, a living body 10 as the model of the signal source illustrated in FIG. 10 and illustrating a state when each electrode is arranged on a surface of the cylindrical living body 10.

Figure 11:
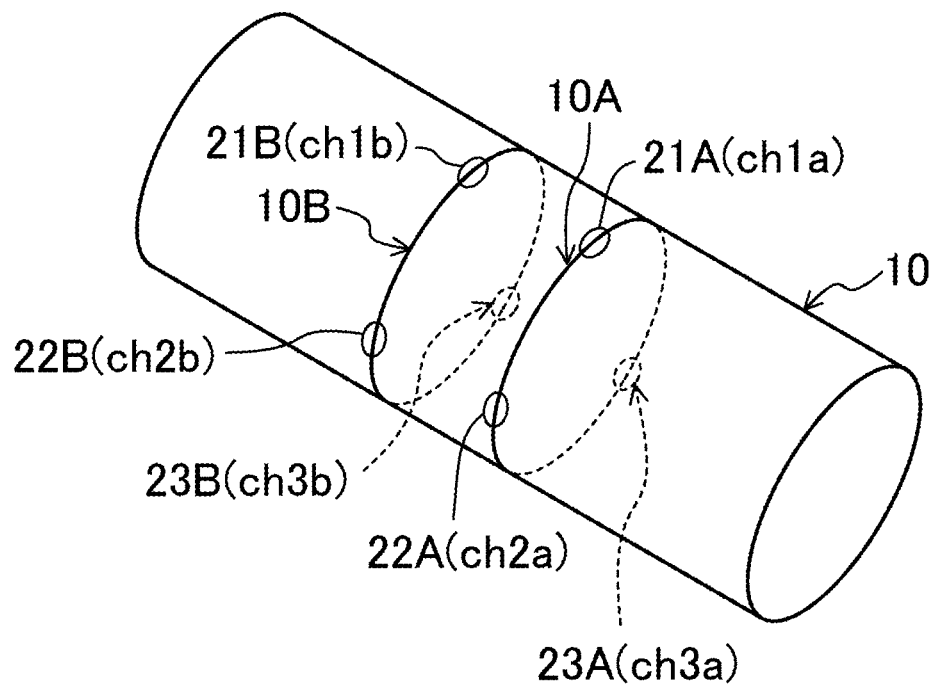
FIG. 11 is a view of arrangement of the electrodes on a surface of a living body.

As illustrated in FIG. 11, in the present embodiment, three electrodes (21A, 22A, 23A) are arranged on the surface of the living body 10, and other three electrodes (21B, 22B, 23B) each paired with three electrodes are arranged in the vicinity of each electrode. The electrodes paired with each other are arranged at positions parallel to the direction of the muscle fiber 40. Moreover, the electrodes (21A, 22A, 23A), (21B, 22B, 23B) forming three pairs are arranged on circumferences 10A, 10B of the surface of the living body 10 to surround the multiple muscle fibers 40. The circumference 10A has a cut plane having a section along an A-A line illustrated in FIG. 10, and the circumference 10B has a cut plane having a section along a B-B line.

Figure 12:
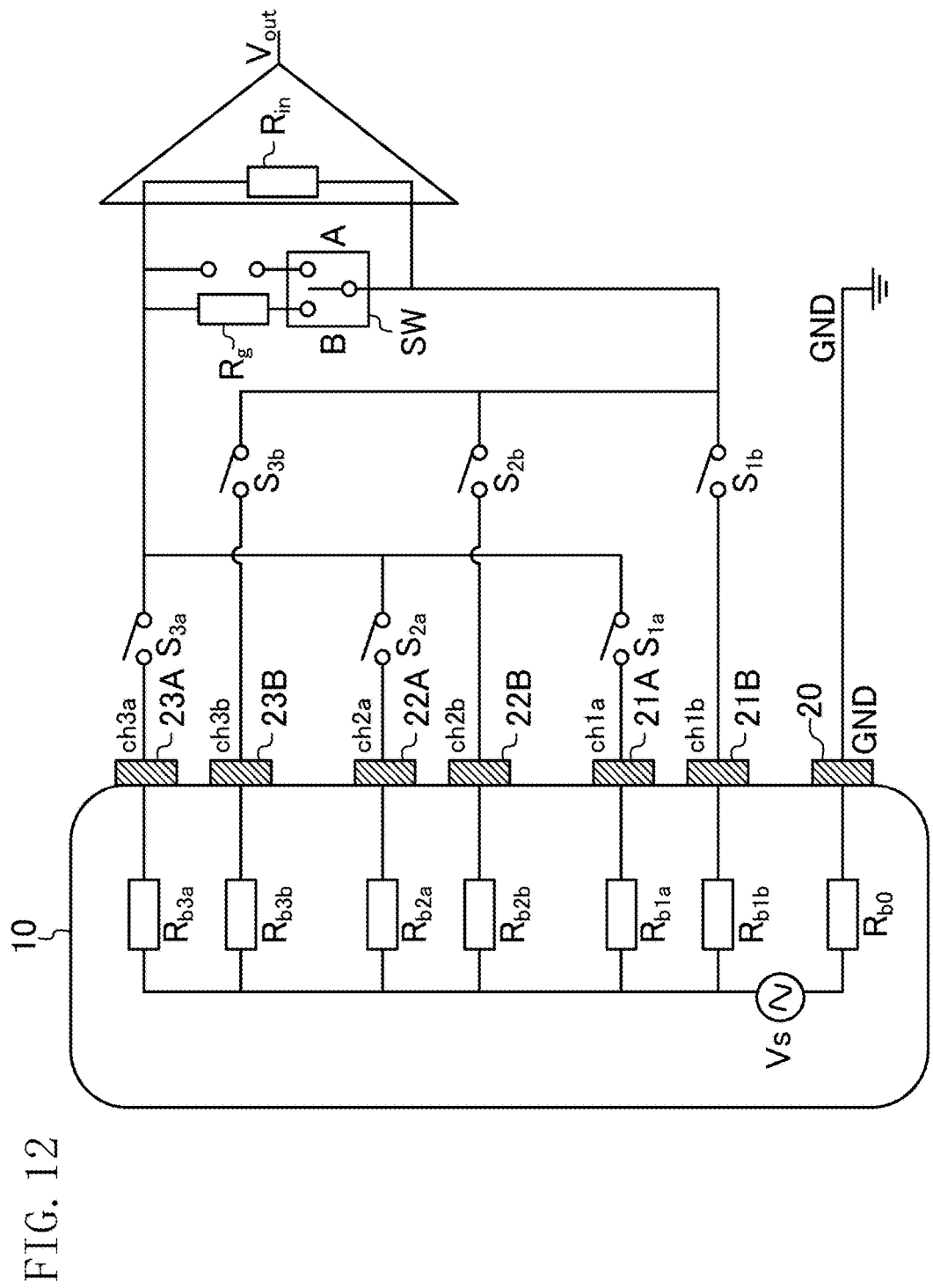
FIG. 12 is an electric network diagram for describing an in-vivo signal source detection method in a third embodiment of the present invention.

FIG. 12 is an electric network diagram for describing the method for detecting the position of the signal source in the living body by means of electrode arrangement illustrated in FIG. 11.

As illustrated in FIG. 12, the three pairs of electrodes (21A, 22A, 23A), (21B, 22B, 23B) are arranged on the surface of the living body 10. Moreover, a first external resistor and a second external resistor configured alternately switchable are connected in parallel between the electrodes (21A, 21B), (22A, 22B), (23A, 23B) forming each pair. Note that in the present embodiment, a resistance value of the first external resistor is, as in the first embodiment, infinite and a resistance value of the second external resistor is Rg. Moreover, in the present embodiment, a ground electrode 20 is arranged on the surface of the living body 10 to serve as a ground potential.

As illustrated in FIG. 12, a switch $S_{1a}$, $S_{2a}$, $S_{3a}$, $S_{1b}$, $S_{2b}$, $S_{3b}$ is arranged between each electrode (21A, 22A, 23A), (21B, 22B, 23B) and a difference amplifier 30. By sequentially bringing the switches $S_{1a}$, $S_{2a}$, $S_{3a}$, $S_{1b}$, $S_{2b}$, $S_{3b}$ into conduction as illustrated in FIG. 13, voltages generated between the electrode 21A and the electrode 21B, between the electrode 22A and the electrode 22B, and between the electrode 23A and the electrode 23B are measured as an output voltage Vout of the difference amplifier 30. The electrodes are, by a switching section SW, switchable between a case where no external resistor is connected and a case where the external resistor Rg is connected. Thus, each of the switching section SW and the switches $S_{1a}$, $S_{2a}$, $S_{3a}$, $S_{1b}$, $S_{2b}$, $S_{3b}$ is switched as illustrated in FIG. 13 (steps 1 to 6), and in this manner, first voltages $V_{1a1b}$, $V_{2a2b}$, $V_{3a3b}$ each generated between the electrodes when no external resistor Rg is connected between the electrodes and second voltages $V'_{1a1b}$, $V_{2a2b}$, $V_{3a3b}$ each generated between the electrodes when the external resistor Rg is connected between the electrodes are measured. Note that in FIG. 12, the electrodes (21A, 22A, 23A), (21B, 22B, 23B) are each indicated as channels ($ch_{1a}$, $ch_{2a}$, and $ch_{3a}$), ($ch_{1b}$, $ch_{2b}$, and $ch_{3b}$).

At the step 1 illustrated in FIG. 13, the first voltage (when no external resistor is connected) $V_{1a1b}$ generated between the electrode 21A and the electrode 21B (between the channels $ch_{1a}$, $ch_{1b}$) is given by Equation (3-1).

[Equation 25]

$$V_{out} = V_{1a1b} = V_s \quad \text{(Equation 3-1)}$$

On the other hand, at the step 4, the second voltage (when the external resistor Rg is connected) $V'_{1a1b}$ generated between the electrode 21A and the electrode 21B (between the channels $ch_{1a}$, $ch_{1b}$) is given by Equation (3-2) if an input resistance $R_{in}$ of the amplifier 30 is extremely high.

[Equation 26]

$$V_{out} = V'_{1a1b} = \frac{R_g}{R_{b1a} + R_{b1b} + R_g} \quad \text{(Equation 3-2)}$$

In this equation, $R_{b1a}$ and $R_{b1b}$ represent an internal resistance between the signal source Vs in the living body 10 and the electrode 21A (the channel $ch_{1a}$) and an internal resistance between the signal source Vs and the electrode 21B (the channel $ch_{1b}$).

From Equations (3-1), (3-2), a ratio (an attenuation ratio) $V'_{1a1b}/V_{1a1b}$ between the first voltage $V_{1a1b}$ and the second voltage $V'_{1a1b}$ generated between the electrode 21A and the electrode 21B (between the channels $ch_{1a}$, $ch_{1b}$) is given by Equation (3-3).

[Equation 27]

$$\frac{V'_{1a1b}}{V_{1a1b}} = \frac{R_g}{R_{b1a} + R_{b1b} + R_g} \quad \text{(Equation 3-3)}$$

Similarly, a ratio (an attenuation ratio) $V'_{2a2b}/V_{2a2b}$ between the first voltage $V_{2a2b}$ and the second voltage $V'_{2a2b}$ generated between the electrode 22A and the electrode 22B (between the channels $ch_{2a}$, $ch_{2b}$) and a ratio (an attenuation ratio) $V'_{3a3b}/V_{3a3b}$ between the first voltage $V_{3a3b}$ and the second voltage $V'_{3a3b}$ generated between the electrode 23A and the electrode 23B (between the channels $ch_{3a}$, $ch_{3b}$) are each given by Equations (3-4), (3-5).

[Equation 28]

$$\frac{V'_{2a2b}}{V_{2a2b}} = \frac{R_g}{R_{b2a} + R_{b2b} + R_g} \quad \text{(Equation 3-4)}$$

[Equation 29]

$$\frac{V'_{3a3b}}{V_{3a3b}} = \frac{R_g}{R_{b3a} + R_{b3b} + R_g} \quad \text{(Equation 3-5)}$$

In these equations, $R_{b2a}$ and $R_{b2b}$ represent an internal resistance between the signal source Vs in the living body 10 and the electrode 22A ($ch_{2a}$) and an internal resistance between the signal source Vs and the electrode 22B ($ch_{2b}$). Moreover, $R_{b3a}$ and $R_{b3b}$ represent an internal resistance between the signal source Vs in the living body 10 and the electrode 23A ($ch_{3a}$) and an internal resistance between the signal source Vs and the electrode 23B ($ch_{3b}$).

Assuming that conductivity inside the living body 10 is uniform, the sum of the internal resistances ($R_{b1a}+R_{b1b}$) is considered to be proportional to the sum ($F_{1a}+F_{1b}$) of a distance $F_{1a}$ between the electrode 21A and the signal source Vs and a distance $F_{1b}$ between the electrode 21B and the signal source Vs. Thus, from Equations (3-3), (3-4), (3-5), the sums ($F_{1a}+F_{1b}$), ($F_{2a}+F_{2b}$), ($F_{3a}+F_{3b}$) of the distances between each electrode and the signal source Vs are each given by Equations (3-6), (3-7), (3-8).

[Equation 30]

$$F_{1a} + F_{1b} = \gamma(R_{b1a} + R_{b1b}) = \gamma\left(\frac{V_{1a1b}}{V'_{1a1b}} - 1\right)R_g \quad \text{(Equation 3-6)}$$

[Equation 31]

$$F_{2a} + F_{2b} = \gamma(R_{b2a} + R_{b2b}) = \gamma\left(\frac{V_{2a2b}}{V'_{2a2b}} - 1\right)R_g \quad \text{(Equation 3-7)}$$

[Equation 32]

$$F_{3a} + F_{3b} = \gamma(R_{b3a} + R_{b3b}) = \gamma\left(\frac{V_{3a3b}}{V'_{3a3b}} - 1\right)R_g \quad \text{(Equation 3-8)}$$

In these equations, γ is a proportional constant between an internal resistance $R_{bia}$ and a distance $F_{ia}$ (i=1, 2, 3), and is defined by the conductivity of the living body 10, for example.

In the present embodiment, the electrodes (21A, 21B), (22A, 22B), (23A, 23B) forming each pair are arranged close to each other. Moreover, three pairs of the electrodes (21A, 22A, 23A), (21B, 22B, 23B) are arranged at positions parallel to the direction of the muscle fiber 40. It is assumed that the signal source Vs has a uniform potential along the muscle fiber 40, and therefore, it is assumed that the internal resistance between each electrode and the signal source Vs is uniform. Thus, the following equation (3-9) is satisfied.

[Equation 33]

$$R_{b1} = R_{b1a} = R_{b1b}$$

$$R_{b2} = R_{b2a} = R_{b2b}$$

$$R_{b3} = R_{b3a} = R_{b3b} \quad \text{(Equation 3-9)}$$

Figure 14:
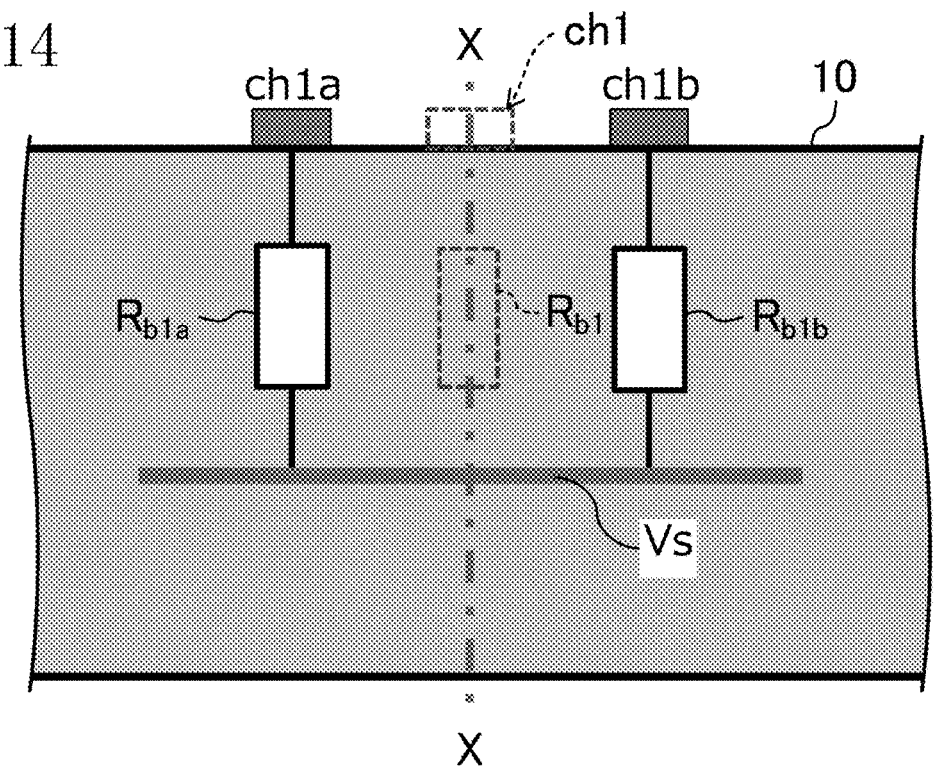
FIG. 14 is a view of arrangement of the electrodes on a surface of a living body.
Figure 15:
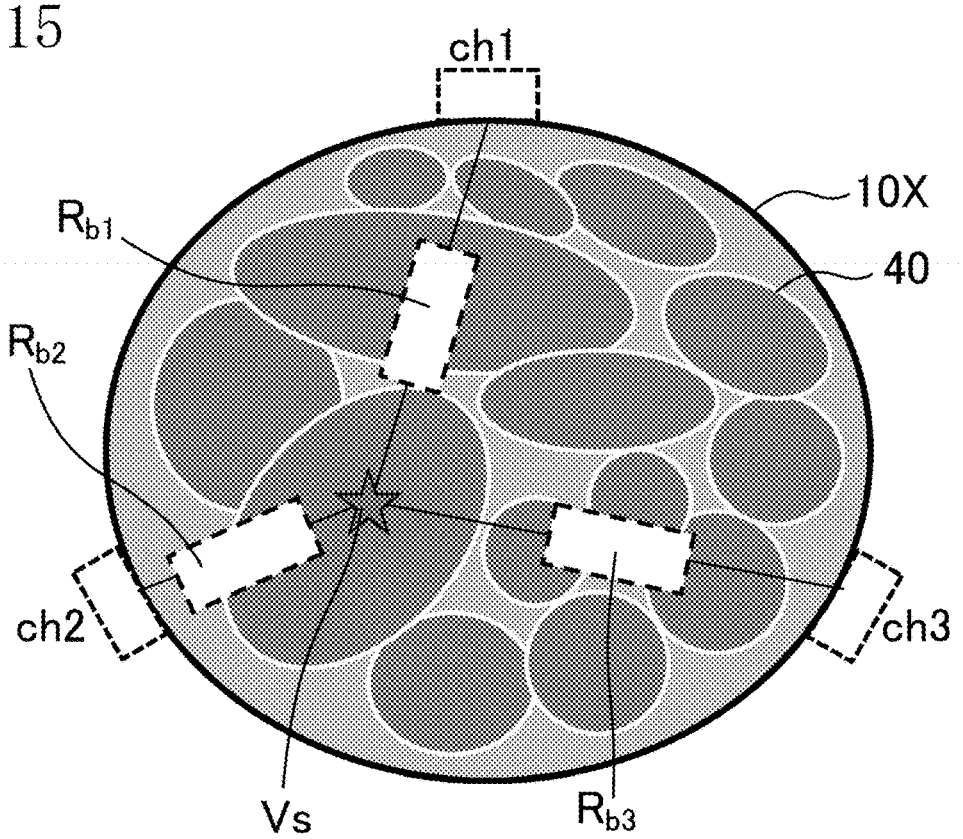
FIG. 15 is a view for describing the method for detecting the position of a signal source.

Thus, as illustrated in, e.g., FIG. 14, the pair of electrodes ($ch_{1a}$, $ch_{1b}$) arranged on the surface of the living body 10 can be represented as a virtual electrode ($ch_1$) arranged in the middle between these electrodes. That is, as illustrated in FIG. 15, the pairs of electrodes ($ch_{1a}$, $ch_{1b}$), ($ch_{2a}$, $ch_{2b}$), ($ch_{3a}$, $ch_{3b}$) are equivalent to the virtual electrodes ($ch_1$, $ch_2$, $ch_3$) arranged on a circumference 10X having a cut plane with a section along an X-X line illustrated in FIG. 14. Note that in this case, an internal resistance between each virtual electrode ($ch_1$, $ch_2$, $ch_3$) and the signal source Vs can be represented as $R_{b1}$, $R_{b2}$, $R_{b3}$.

Moreover, the above-described equation (3-9) is satisfied, and therefore, it is assumed that the same distance between each electrode and the signal source Vs is given. Thus, the following equation (3-10) is satisfied.

[Equation 34]

$$F_1 = F_{1a} = F_{1b}$$

$$F_2 = F_{2a} = F_{2b}$$

$$F_3 = F_{3a} = F_{3b} \quad \text{(Equation 3-10)}$$

Thus, the above-described equations (3-6), (3-7), (3-8) are each represented by the following equations (3-11), (3-12), (3-13).

[Equation 35]

$$F_1 = \frac{\gamma}{2}\left(\frac{V_{1a1b}}{V'_{1a1b}} - 1\right)R_g \quad \text{(Equation 3-11)}$$

[Equation 36]

$$F_2 = \frac{\gamma}{2}\left(\frac{V_{2a2b}}{V'_{2a2b}} - 1\right)R_g \quad \text{(Equation 3-12)}$$

[Equation 37]

$$F_3 = \frac{\gamma}{2}\left(\frac{V_{3a3b}}{V'_{3a3b}} - 1\right)R_g \quad \text{(Equation 3-13)}$$

Figure 16:
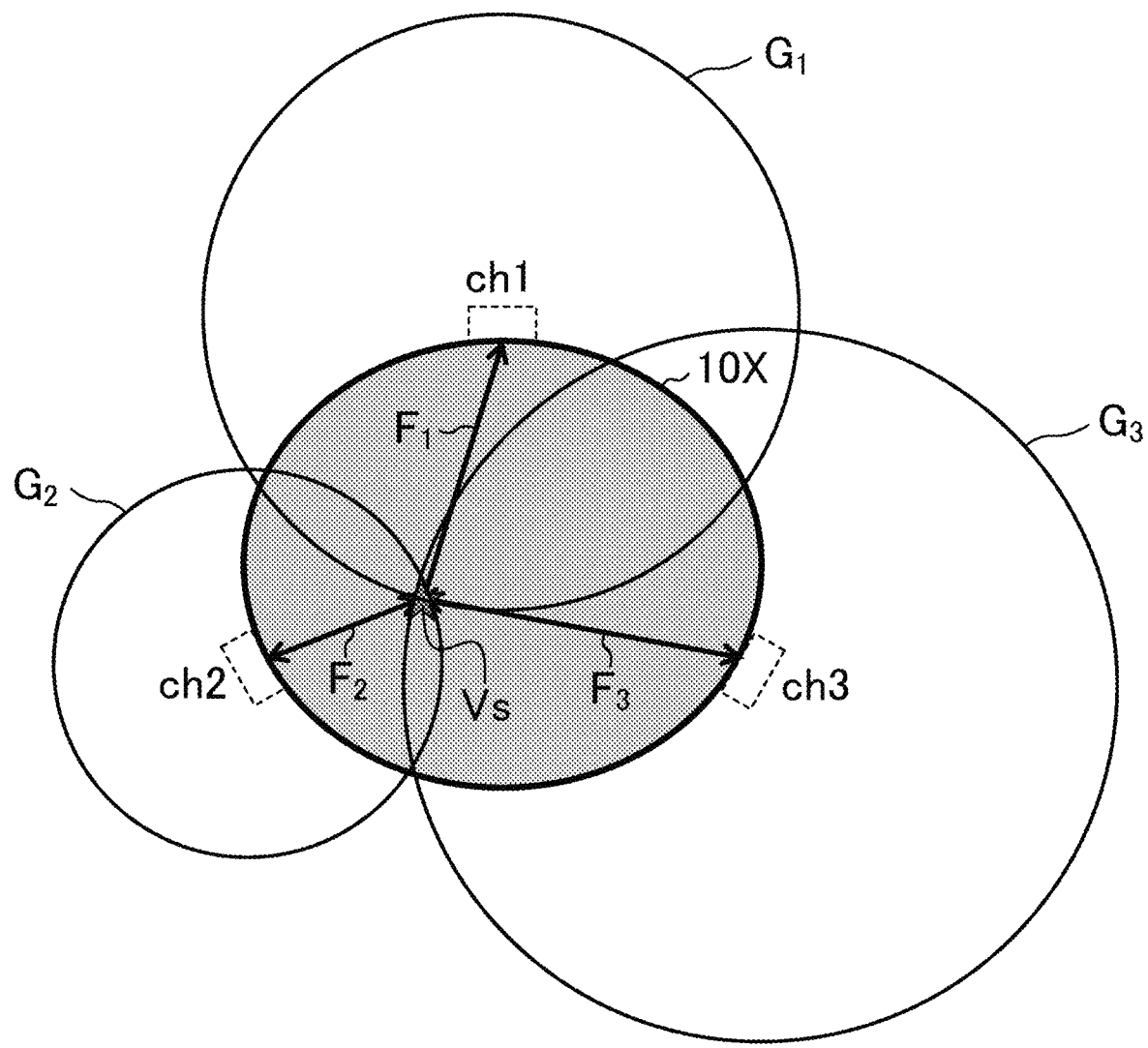
FIG. 16 is a view for describing the method for detecting the position of the signal source.

As illustrated in Equations (3-11), (3-12), (3-13), each of the distances $F_1$, $F_2$, $F_3$ is expressed as the function of the reciprocal of the attenuation ratio ($V'_{1a1b}/V_{1a1b}$, $V'_{2a2b}/V_{2a2b}$, $V'_{3a3b}/V_{3a3b}$). As illustrated in FIG. 16, the signal source Vs is considered to be present at the point of intersection of circles $G_1$, $G_2$, $G_3$ each having radiuses $F_1$, $F_2$, $F_3$ about the virtual electrodes ($ch_1$, $ch_2$, $ch_3$). When the position coordinates of each virtual electrode ($ch_1$, $ch_2$, $ch_3$) is ($a_1$, $b_1$), ($a_2$, $b_2$), ($a_3$, $b_3$), the circles $G_1$, $G_2$, $G_3$ are each represented by the following equations (1-14), (1-15), (1-16).

[Equation 38]

$$\sqrt{(x-a_1)^2+(y-b_1)^2}=F_1 \quad \text{(Equation 3-14)}$$

[Equation 39]

$$\sqrt{(x-a_2)^2+(y-b_2)^2}=F_2 \quad \text{(Equation 3-15)}$$

[Equation 40]

$$\sqrt{(x-a_3)^2+(y-b_3)^2}=F_3 \quad \text{(Equation 3-16)}$$

Thus, using $F_1$, $F_2$, $F_3$ obtained from Equations (3-11), (3-12), (3-13), three simultaneous equations represented by the following equation (3-17) can be obtained.

[Equation 41]

$$\sqrt{(x-a_1)^2+(y-b_1)^2} = \frac{\gamma}{2}\left(\frac{V_{1a1b}}{V'_{1a1b}}-1\right)R_g$$

$$\sqrt{(x-a_2)^2+(y-b_2)^2} = \frac{\gamma}{2}\left(\frac{V_{2a2b}}{V'_{2a2b}}-1\right)R_g \quad \text{(Equation 3-17)}$$

$$\sqrt{(x-a_3)^2+(y-b_3)^2} = \frac{\gamma}{2}\left(\frac{V_{3a3b}}{V'_{3a3b}}-1\right)R_g$$

Unknown numbers of three simultaneous equations represented by Equation (3-17) are three numbers including the two-dimensional coordinates (x, y) of the signal source Vs and the constant γ. Thus, three simultaneous equations represented by Equation (3-12) are solved so that the two-dimensional coordinates (x, y) of the signal source Vs and the constant γ can be obtained. Note that the coordinates of a midpoint between the electrodes (21A, 21B), (22A, 22B), (23A, 23B) forming each pair is preferably used as the position coordinates ($a_1$, $b_1$), ($a_2$, $b_2$), ($a_3$, $b_3$) of each virtual electrode ($ch_1$, $ch_2$, $ch_3$). Moreover, in a case where the electrodes (21A, 21B), (22A, 22B), (23A, 23B) forming each pair are arranged close to each other, even when the position coordinates of either one of the electrodes are used, almost no influence is on the accuracy of obtaining the two-dimensional coordinates (x, y) of the signal source Vs.

As described above, according to the present embodiment, three pairs of electrodes (21A, 22A, 23A), (21B, 22B, 23B) are arranged at the positions parallel to the direction of the muscle fiber 40, and therefore, it can be assumed that the same internal resistance between each electrode and the signal source Vs is given. Thus, when the two-dimensional coordinates (x, y) of the signal source Vs are obtained, an internal resistance $R_{b0}$ between the signal source Vs and the ground electrode 20 is not necessarily obtained in advance. In addition, three simultaneous equations represented by Equation (3-12) are solved so that the proportional constant γ between the internal resistance ($R_{bia}+R_{bib}$) and the distance ($F_{ia}+F_{ib}$) (i=1, 2, 3) can be obtained. Thus, the two-dimensional coordinates of the signal source Vs in the living body can be easily obtained. In particular, even in the case of, e.g., monitoring muscle fibers acting during training, the muscle fibers acting in the living body can be easily detected.

Note that in the present embodiment, in the case of different distances among the pairs of electrodes, when there is influence of disturbance, the attenuation ratios ($V'_{1a1b}/V_{1a1b}$, $V'_{2a2b}/V_{2a2b}$, $V'_{3a3b}/V_{3a3b}$) change. For this reason, for uniform measurement environment among the virtual electrodes, the same distance among all pairs of electrodes is preferably given.

The present invention has been described above with reference to the preferred embodiments, but such description is not a limited matter. Needless to say, various modifications can be made. For example, in the above-described embodiments, three electrodes 21, 22, 23 are arranged on the circumference of the surface of the living body 10, but three or more electrodes may be arranged for more enhancing the accuracy of detection of the position of the signal source Vs.

Moreover, arrangement locations of three electrodes 21, 22, 23 on the circumference of the surface of the living body 10 in the above-described embodiments are not specifically limited. However, when the electrodes 21, 22, 23 are arranged at positions close to each other, the first voltage $V_i$ (i=1, 2, 3) and the second voltage $V'_i$ (i=1, 2, 3) generated between each electrode and the ground potential or between the electrodes are values close to each other. For this reason, the signal source in the living body is detected based on a slight difference among three ratios $V_i/V'_i$ (i=1, 2, 3). In this case, when slight noise is in measurement values of the first and second voltages $V_i$, $V'_i$, the voltage ratio $V_i/V'_i$ is buried in the noise, and therefore, there is a probability that it is difficult to accurately detect the position of the signal source. Thus, three electrodes 21, 22, 23 are preferably arranged apart from each other to the maximum extent possible. In particular, three electrodes 21, 22, 23 are more preferably arranged at regular intervals on the circumference of the surface of the living body 10. Thus, a difference between the measurement values of the first and second voltages $V_i$, $V'_i$ is greater, and therefore, the position of the signal source can be more accurately detected even when slight noise is in the measurement values.

Further, in the above-described third embodiment, the other three electrodes (21B, 22B, 23B) each paired with three electrodes (21A, 22A, 23A) are arranged at the positions parallel to the direction of the muscle fiber 40 with respect to three electrodes (21A, 22A, 23A). However, each electrode (21B, 22B, 23B) may be arranged close to the electrode (21A, 22A, 23A) on the same circumference.

DESCRIPTION OF REFERENCE CHARACTERS

10 Living Body
10A, 10B, 10X Circumference
20 Ground Electrode
21 First Electrode (Channel $ch_1$)
22 Second Electrode (Channel $ch_2$)
23 Third Electrode (Channel $ch_1$)
30 Difference Amplifier
40 Muscle Fiber
40a Activity Site

The invention claimed is:

1. An in-vivo signal source detection method for detecting a position of a signal source in a living body by a voltage generated at an electrode arranged on a surface of the living body, wherein
at least three electrodes are arranged on a circumference of the surface of the living body to surround multiple muscle fibers, and a first external resistor and a second external resistor are alternately switchably connected in parallel between each electrode and a ground potential or between ones of the electrodes,
a first voltage $V_i$ (i=1, 2, 3) generated when the first external resistor is connected to between each electrode and the ground potential or between ones of the electrodes and a second voltage $V'_i$ (i=1, 2, 3) generated when the second external resistor is connected to between each electrode and the ground potential or between ones of the electrodes are measured, and
a ratio $V_i/V'_i$ (i=1, 2, 3) is calculated from the first voltage $V_i$ and the second voltage $V'_i$, and the position of the signal source in the living body is detected based on three ratios $V_i/V'_i$ (i=1, 2, 3).

2. The method of claim 1, wherein
when the three electrodes arranged on the circumference of the surface of the living body are a first electrode, a second electrode, and a third electrode, the first external resistor and the second external resistor are alternately switchably connected in parallel between the first and second electrodes, between the second and third electrodes, and between the third and first electrodes, and
when the first voltage $V_i$ generated at each electrode when the first external resistor is connected in parallel between ones of the electrodes is $V_{12}$, $V_{23}$, $V_{31}$ and the second voltage $V'_i$ generated at each electrode when the second external resistor is connected in parallel between ones of the electrodes is $V'_{12}$, $V'_{23}$, $V'_{31}$, ratios $V_{12}/V'_{12}$, $V_{21}/V'_{21}$, $V_{31}/V'_{31}$ are calculated from the first voltages $V_{12}$, $V_{23}$, $V_{31}$ and the second voltages $V'_{12}$, $V'_{23}$, $V'_{31}$, and the position of the signal source in the living body is detected based on the three ratios $V_{12}/V'_{12}$, $V_{21}/V'_{21}$, $V_{31}/V'_{31}$.

3. The method of claim 1, wherein
other three electrodes each paired with the three electrodes are further arranged close to the three electrodes arranged on the circumference of the surface of the living body,
the first external resistor and the second external resistor are alternately switchably connected in parallel between the electrodes forming each pair,
a first voltage $V_i$ (i=1, 2, 3) generated when the first external resistor is connected to between the electrodes forming each pair and a second voltage $V'_i$ (i=1, 2, 3) generated when the second external resistor is connected to between the electrodes forming each pair, and
a ratio $V_i/V'_i$ (i=1, 2, 3) is calculated from the first voltage $V_i$ and the second voltage $V'_i$, and the position of the signal source in the living body is detected based on three ratios $V_i/V'_i$ (i=1, 2, 3).

4. The method of claim 1, wherein
either one of the first external resistor or the second external resistor has an infinite resistance value.

5. The method of claim 1, wherein
the three electrodes arranged on the circumference of the surface of the living body are arranged at regular intervals on the circumference.

6. The method of claim 3, wherein
the other three electrodes each paired with the three electrodes are arranged parallel to a direction of the muscle fibers with respect to the three electrodes.

7. The method of claim 6, wherein
an identical distance between the electrodes forming each pair is given.

8. An in-vivo signal source detection device for detecting a position of a signal source in a living body by a voltage generated at an electrode arranged on a surface of the living body, comprising:
an electrode unit being attachable to the surface of the living body and configured such that at least three electrodes are coupled to each other in one direction;
a connection section configured to alternately switchably connect a first external resistor and a second external resistor in parallel between each electrode and a ground potential or between ones of the electrodes;
a measurement section configured to measure, in a state in which the electrode unit is arranged on the surface of the living body, a first voltage $V_i$ (i=1, 2, 3) generated when the first external resistor is connected to between each electrode and the ground potential or between ones of the electrodes by the connection section and a second voltage $V'_i$ (i=1, 2, 3) generated when the second external resistor is connected to between each electrode and the ground potential or between ones of the electrodes by the connection section; and
a detection section configured to calculate a ratio $V_i/V'_i$ (i=1, 2, 3) from the first voltage $V_i$ and the second voltage $V'_i$ to detect the position of the signal source in the living body based on three ratios $V_i/V'_i$ (i=1, 2, 3),
wherein the electrode unit is configured such that the at least three electrodes are arranged in a circumferential direction of the surface of the living body to surround multiple muscle fibers.

9. The device of claim 8, wherein
a second electrode unit having other three electrodes each paired with the three electrodes is further arranged close to the electrodes of the electrode unit.

10. The method of claim 2, wherein
either one of the first external resistor or the second external resistor has an infinite resistance value.

11. The method of claim 3, wherein
either one of the first external resistor or the second external resistor has an infinite resistance value.

12. The method of claim 2, wherein
the three electrodes arranged on the circumference of the surface of the living body are arranged at regular intervals on the circumference.

13. The method of claim 3, wherein
the three electrodes arranged on the circumference of the surface of the living body are arranged at regular intervals on the circumference.

* * * * *